(12) United States Patent
Vierto-Oja (10) Patent No.: US 6,254,546 B1
(45) Date of Patent: Jul. 3, 2001

(54) METHOD TO DETERMINE VENTILATION-PERFUSION AND VENTILATION-VOLUME DISTRIBUTIONS OF THE LUNGS

(75) Inventor: Hanna Vierto-Oja, Espoo (FI)

(73) Assignee: Instrumentarium Corporation, Helsinki (FI)

(*) Notice: Subject to any disclaimer, the term of this patent is extended or adjusted under 35 U.S.C. 154(b) by 0 days.

(21) Appl. No.: 09/457,065

(22) Filed: Dec. 7, 1999

(51) Int. Cl.$^7$ .................................................. A61B 5/08
(52) U.S. Cl. ........................................ 600/529; 600/532
(58) Field of Search ............................. 600/529, 531, 600/532, 533, 537, 538

(56) References Cited

U.S. PATENT DOCUMENTS

| | | | |
|---|---|---|---|
| 4,363,327 | * 12/1982 | Clark ..................................... | 600/532 |
| 5,606,976 | * 3/1997 | Marshall et al. ...................... | 600/529 |
| 6,042,550 | * 3/2000 | Haryadi et al. ....................... | 600/504 |

OTHER PUBLICATIONS

Wagner, P. D.; Saltzman, H. A.; West, J. B.; Measurement of continuous distributions of ventilation–perfusion ratios: theory, Journal of Applied Physiology, vol. 36, No. 5, May 1974, pp 588–599.

Roca, J. and Wagner, P. D., Principles and information content of the multiple inert gas elimination technique, Thorax 1993; 49:815–824.

Sackner, M. A., Measurement of cardiac output by alveolar gas exchange, In: Fishman A. P. et al., eds. Handbook of Physiology, Section 3, vol. IV, Bethesda: American Physiological Society, 1987, pp. 233–255.

Kennedy, R.R. and Baker A. B., Solubility characteristics of the ideal agent for measurement of cardiac output by soluble gas uptake methods, British Journal of Anaesthesia 1993: 71:398–402.

Overland, E. S. et al., Measurement of pulmonary tissue volume and blood flow in persons with normal and edematous lungs, Journal of Applied Physiological, 1981; 51(5):1375–1383.

Jonmarker C. et al., Measurement of Functional Residual Capacity by Sulfur Hexafluoride Washout, Anesthesiology 1985, vol. 63, No. 1:89–95.

* cited by examiner

*Primary Examiner*—Cary O'Connor
*Assistant Examiner*—Navin Natnithithadha
(74) *Attorney, Agent, or Firm*—Andrus, Sceales, Starke & Sawall, LLP (57) ABSTRACT

A method for determining the tidal volume ($V_t$) distribution in the lungs of a subject. The distribution is made among a plurality of compartments (i). Each compartment has an assigned tidal volume ($V_{ti}$)/perfusion ($Q_i$) ratio and an assigned tidal volume ($V_{ti}$)/compartmental volume ($V_{ai}$) ratio so that the compartments, collectively, cover a range of ventilation/perfusion ratio ($V_t/Q$) values and ventilation/volume ($V_t/V_a$) ratio values. The subject inspires a bolus of analytical gases in his/her tidal volume of breathing gases. The analytical gases of the bolus have differing solubilities in the blood of the subject and are inspired in known amounts. The concentrations of the analytical gases expired by the subject are measured, preferably in a plurality of breaths. The expired analytical gas concentrations are expressed as a function dependent on the inspired bolus amounts, the ventilation/perfusion ratios, the ventilation/volume ratios, and the compartmental tidal volumes ($V_{ti}$). This expression is transformed into one that can be minimized using the method of Lagrange multipliers to obtain the compartmental tidal volume distribution, and the ventilation/perfusion and ventilation/volume distributions.

37 Claims, 5 Drawing Sheets

METHOD TO DETERMINE VENTILATION-PERFUSION AND VENTILATION-VOLUME DISTRIBUTIONS OF THE LUNGS

BACKGROUND OF THE INVENTION

During breathing, the respiratory system transports breathing gases to the lungs, carries out a gas exchange in which oxygen ($O_2$) is supplied to the blood and carbon dioxide ($CO_2$) is removed from the blood, and returns the breathing gases to the source. Typically, the breathing gases are those found in air and are taken from, and returned to, the atmosphere through the mouth and nose of a subject by his/her natural breathing action. However, a mechanical ventilator may be employed to assist or supplant the natural breathing action by supplying/receiving breathing gases through a mask, endotracheal tube, or tracheotomy tube.

The amount of breathing gases breathed in and out of the lungs in normal breathing is termed the tidal volume ($V_T$). This is typically 400–700 milliliters (ml) per breath. The lungs also have a residual volume beyond that participating in the normal breathing action. This volume is termed the functional residual capacity (FRC) and is the volume of breathing gases remaining in the lungs at the end of a normal exhalation or expiration. For a typical subject, the functional residual capacity may be 700–3500 ml.

The foregoing and other lung volumes are formed in the alveoli and breathing passages of the lung. The alveoli are small air sacs at the end of the respiratory airway, each of which is served by a pulmonary capillary. The major function of the alveoli is to carry out the gas exchange between breathing gases supplied by the respiratory system and the blood in the circulatory system.

For effective gas exchange between the breathing gas in the lungs and the blood in the capillaries, there must be adequate amounts of both ventilation (alveolar breathing gases) and perfusion (capillary blood flow). If either is impaired, gas exchange will suffer. For example, where there is ventilation without perfusion, a unit of "dead space" exists in the lungs and gas exchange is lessened or prevented. An example of this is the presence of a pulmonary embolus that prevents blood flow through a pulmonary capillary. Similarly, where there is no ventilation of a portion of the lung but perfusion is present, a "shunt" is said to exist and gas exchange is also lessened or prevented. This may occur with a collapse of alveoli in the lungs (atelectasis). The foregoing represent extreme cases. In most situations, any losses in gas exchange efficiency are due to reductions, rather than blockage, in ventilation or perfusion.

A convenient way to express the effectiveness of gas exchange occurring in a subject's lungs is by the ratio of the amount of air (V) respired in the lungs (ventilation) to the blood flow (Q) occurring in the lungs (perfusion). This ratio is termed the ventilation/perfusion or "V/Q" ratio. A low ventilation/perfusion ratio (shunt-like condition) or a high ventilation/perfusion ratio (dead space-like condition) both result in lessened gas exchange and lower oxygen levels in the blood. Knowing the V/Q ratio is useful in preventing hypoxia in the subject and in diagnosing conditions, such as, pulmonary embolism, pulmonary infarction, emphysema, fibrosis, bronchiectasis, as well as in the preoperative assessment of candidates for surgical resection of, for example, a thoracic malignancy.

A ventilation/perfusion ratio can be obtained from a subject's tidal volume of breathing gases and pulmonary blood flow. However, the lungs contain millions of alveoli, each of which have individual gas exchange characteristics due to anatomy, disease, aging, or for other reasons. An overall V/Q ratio obtained from tidal volume and pulmonary blood flow is thus a rather gross measure of the complexity and range in efficacy of the gas exchange actually occurring in a subject's lungs. V/Q data that provides information regarding the range of V/Q ratios found in the lungs and the relative presence or "distribution" of the various V/Q ratios would more precisely reflect the health of the lungs and be much more useful for diagnostic and other purposes. Using a simple example, such data might show that a seemingly normal overall V/Q ratio actually consists of a component of normal V/Q ratios, a portion of high V/Q ratios and a portion of low V/Q ratios. The normal overall V/Q ratio would indicate that adequate oxygenation is occurring whereas knowledge of the distribution of the various V/Q ratios might call this into question.

One way to obtain information regarding the V/Q ratio is to inject a radioactive dye intravenously, and allow it to be carried into the pulmonary vasculature where decreased blood flow, if present, can be seen by x-ray film or a radioactivity detector. For ventilation, radioactive gas is inhaled to similarly produce an image of areas where ventilation is or is not occurring. While this technique is straightforward and simple, it suffers from inaccuracies and it is difficult to determine differing V/Q ratios and the distribution of the range of V/Q ratios.

A more sophisticated technique for determining ventilation/perfusion ratios employs a plurality of different gases, the solubilities of which, in blood, range from very low, for example, sulfur hexafluoride ($SF_6$) to very high, such as acetone. This technique is called the multiple inert gas elimination technique (MIGET). The gases are infused at a constant rate into a peripheral vein of a subject located, for example, in the arm. With the gases absorbed and circulating in the blood stream of the subject, some amount of each gas in the blood undergoes gas exchange in the alveoli of the lungs and is eliminated from the body upon expiration. The relationship between the amount of a particular gas eliminated and the amount of that gas that remains in the blood is governed by the ventilation/perfusion ratio and the solubility of the gas in the blood.

The use of gases with different solubilities permits the range of V/Q ratios and their distribution to be determined. The manner in which this is accomplished is explained in a simplified fashion, as follows. For simplicity, it is assumed that the ventilation is generally uniform throughout the lungs, i.e. is homogeneous, whereas perfusion is not uniform throughout the lungs, i.e. some alveoli have greater perfusion than others. For a gas that is highly soluble in the blood, only a small portion will be exchanged to the alveolar breathing gases because of the tendency for the gas to remain in the blood. The exchange that does occur will take place in those alveoli which have high perfusion. Thus the presence of a high blood solubility gas in the respiratory and circulatory systems of the subject, in effect, divides the alveoli of the lungs into two categories. The first category is those that have high perfusion. The second category is those that do not have high perfusion. This, in turn, establishes two V/Q ratio categories: first, alveoli having a lower V/Q ratio; and second, alveoli that do not have the lower V/Q ratio. The amounts of the gas found in the expired air of the subject come from alveoli of the first category (high perfusion).

For a gas that has a low solubility in the blood, a large portion of the gas will tend to be exchanged to the alveolar breathing gases and discharged on expiration. The exception will be alveoli having low perfusion. A low blood solubility gas will also divide the lungs into two categories: those with low perfusion; and those not having low perfusion; each with different V/Q ratios.

The same phenomenon occurs for each gas of differing solubility with the division into categories occurring at a different V/Q ratio. By subjecting the combined blood gas-expiration gas data for all gases to appropriate mathematical analysis, the range of V/Q ratios in a subject's lungs and the distribution of the V/Q ratios can be determined.

Because of the mathematical treatment used to obtain such quantitative results and to model the lungs, the categorizations of lung characteristics resulting from the mathematical treatment are often expressed as "compartments." However, it is to be understood that such compartmental descriptions are analytical concepts that do not necessarily have a direct correlation to anatomical portions of the lungs, such as lobes.

Due to its ability to obtain the information described above, the MIGET has received widespread acceptance as a tool for diagnosing the condition of the lungs and efficacy of gas exchange therein. The MIGET is further described in Wagner P. D., Salzman H. A., West J. B., Measurement of continuous distribution of ventilation-perfusion ratios: theory, J Appl Physiol 1974; 36:588–99 and Roca J. and Wagner P. D., Principles and information content of the multiple inert gas elimination technique, Thorax 1993; 49:815–824.

However, while useful, the multiple inert gas elimination technique is very laborious and invasive. The technique requires infusion of the gas mixture into a vein of one arm of the subject, collection of arterial and venous samples from the other arm of the subject, and measurement of the concentration of each of the gases in the expired breathing gases of the subject. It takes a considerable period of time (40 mins.) for physiological equilibrium to be reached, after which the blood samples and expired concentrations can be taken for use in determining the V/Q ratio information.

Further, because the MIGET is carried out under steady state conditions, there are certain lung characteristics that are not amenable to determination by this technique. For example, another quantification of lung physiology that is useful for diagnostic purposes is ventilation per unit of alveolar gas volume and particularly the distribution of this quantification. This ratio is the relationship of the tidal volume ($V_T$) to the functional residual capacity (FRC) of the lungs. When described on the basis of compartments (i), it is expressed as $V_{ti}/V_{ai}$, functional residual capacity being the sum of the alveolar volumes ($V_{ai}$), i.e. FRC=$\Sigma_i V_{ai}$. The distribution of this quantification indicates how homogeneously the ventilation is distributed in the lungs. For adequate oxygenation, it is desirable to have homogeneous distribution of ventilation in the lung volume. Knowing the $V_t/V_a$ distribution for a given subject is a useful addition to other data concerning the lungs. For example, if the $V_t/V_a$ data is normal but the V/Q data is abnormal, this would tend to indicate that a lung problem lies with perfusion (Q), not ventilation, characteristics. If both distributions are abnormal, the problem may lie with ventilation.

However, because of the steady-state nature of the multiple inert gas elimination technique, it does not give information regarding the ventilation per unit of gas volume ($V_t/V_a$) and its distribution characteristics. Depending on particular diagnostic requirements, this can be a significant limitation.

Other diagnostic information regarding the lung that may be usefull is pulmonary tissue volume and the amount of water (edema) in the lungs. However, it is not possible to determine pulmonary tissue volume or the amount of lung water with the MIGET because, in steady state, the lung tissue and lung water act only as static storages of gas with zero net transfer of gas. With zero net gas transfer, no measurements can be made that would enable these quantities to be determined.

Techniques do exist for determining these quantities using a blood soluble inert gas and an insoluble inert gas. Such techniques can also be used to measure pulmonary blood flow. See Overland E. S. et al., Measurement of pulmonary tissue volume and blood flowing in persons with normal and edematous lungs. J Appln Physiol 1981; 51(6): 1375–1383; Sackner M A, Measurement of cardiac output by alveolar gas exchange. In: Fishman AP et al., eds. Handbook of Physiology, Section 3: Volume IV; Bethesda: American Physiological Society, 1987; 233–255; and Kennedy R R and Baker A B, Solubility characteristics of the ideal agent for measurement of cardiac output by soluble gas uptake methods, Br. J. Anaesth. 1993; 71: 398–402.

In these other techniques for determining lung tissue volume, lung water, and pulmonary blood flow, the lungs are assumed to be homogeneous in nature, i.e., consist of one compartment. However, this means that for subjects with inhomogeneities in either the ventilation/perfusion ratios $(V_i/Q)_i$ distribution or the ventilation/volume ratios $(V_t/V_a)_i$ distribution, the measurements will give false results.

SUMMARY OF THE PRESENT INVENTION

The present invention is, therefore, directed to an improved method for determining physiological characteristics of the lung, such as compartmental tidal volume distribution or other distributions, that possesses advantages over existing methods.

In contrast to the MIGET, the method of the present invention is non-invasive in nature and can be performed in a very short period of time, typically 20 seconds.

In addition to determining compartmental tidal volume distribution, with the present invention, it is possible to measure compartmental ventilation per alveolar gas volume $(V_t/V_a)_i$ and its distribution. This permits a clinician to distinguish among abnormalities in a subject's lungs that originate from inhomogeneities in ventilation, alveolar volume, and/or perfusion in a subject.

The present invention can be easily adapted to accurately measure pulmonary tissue volume and the amount of water in the lungs.

The present invention treats the anatomical dead space in the subject's airway as a serial compartment of the airway. This is a realistic treatment when viewed from the standpoint of anatomy and air flow in the subject's breathing passages. In the multiple inert gas elimination technique, anatomical dead space is treated as a parallel compartment.

Briefly, the present invention is directed to a method for determining the tidal volume ($V_t$) distribution, or other distribution, in the lungs of a subject. The distribution is made among a plurality of compartments (i). When determining distribution of tidal volume, each compartment has an assigned tidal volume ($V_t$)/perfusion (Q) ratio value and an assigned tidal volume ($V_t$)/compartmental volume ($V_a$) ratio value so that the compartments, collectively, cover a range of one or both of ventilation/perfusion ($V_t/Q$) ratio values and/or a range of ventilation/volume ($V_T/V_a$) ratio values.

To carry out the method of the present invention, the subject inspires a bolus of analytical gases in the breathing gases of at least one breath. The analytical gases of the bolus have differing solubilities in the blood of the subject. The concentrations of the analytical gases expired by the subject are measured, preferably in a plurality of breaths.

The expired analytical gas concentrations are expressed as functions dependent on the inspired bolus amounts, the compartmental tidal volumes ($V_{ti}$), ventilation/perfusion ratio, and ventilation/volume ratio. This expression is transformed into an optimization problem which can be solved using a Monte Carlo simulation technique to obtain compartmental tidal volume distribution, the ventilation/perfusion distribution and the ventilation/volume distribution.

Various other features, objects, and advantages of the invention will be made apparent from the following detailed description and the drawings.

DETAILED DESCRIPTION OF THE INVENTION

In the method of the present invention, a bolus of an analytical gas mixture is inspired by the subject. Due to the unique differences between the method of the present invention and that of the MIGET, analytical gases suitable for use in the present invention, may differ from those commonly used in the MIGET. In the MIGET, the gases are placed in a saline solution and infused into the body at a constant rate at very low concentrations. In the method of the present invention, the inspiration of the gases results in much more rapid administration and the gases are delivered in only one or several doses of higher concentration rather than continuously. Gases with low vapor pressure, such as enflurane, are difficult to deliver in precise amounts in the gaseous phase used in the method of the present invention. The use of flammable gases, such as diethyl ether, is unsafe.

For use in carrying out the method of the present invention, the analytical gases should have the following properties. The blood/gas partition coefficient or "solubility" of the gases in blood should range from very low ($\lambda=0.005$) to a sufficiently high value, such as $\lambda>10$. The solubility of a gas, such as an analytical gas, in a liquid, such as blood, may be expressed as the volume of gas dissolved per unit volume of liquid at a given temperature when the liquid is equilibrated with an excess amount of gas of known concentration. The ratio of the gas concentration in the liquid to the concentration of gas in its gaseous phase is termed the partition coefficient ($\lambda$). A description of partition coefficients, and their derivation and use, is contained in H. J. Lowe and E. A. Ernest, *The Qualitative Practice of Anesthesia*, published by Williams and Wilkins, 1981 at pages 28, et seq.

It is preferable, that the gases be selected such that the solubilities of the selected gases are distributed in a desired manner, such as somewhat equally, along a logarithmic scale of the range of solubilities exhibited by the various gases employed in carrying out the method. Or, more simply, gases with low, medium and high solubility should be used. Also, it is desirable that the vapor pressure of the gases be sufficiently high as to permit a mixture of the analytical gases to be stored, prior to administration, in the gaseous phase. And, naturally, the gases should be safe, as by being non-toxic and non-inflammable.

Analytical gases suitable for use in the method of the present invention may include $SF_6$; NO; $CO_2$; $N_2O$; $(CH_3)_2O$; $CH_3OCH:CH_2$, and fluorated hydrocarbons (HFC) 125, 134a, 152a, 227ea, and 32. A typical mixture of bolus gases is shown in the table below. The amount of each analytical gas inspired may be such as to place the inspiratory concentration of each gas at 4% which would correspond to a mean alveolar concentration on the order of 1%.

TABLE 1

| Gas | $\lambda$ |
|---|---|
| Sulfur hexafluoride ($SF_6$) | 0.005 |
| HFC-125 ($CHF_2CF_3$) | 0.20 |
| HFC-32 ($CH_2F_2$) | 1.0 |
| Dimethyl ether $(CH_3)_2O$ | 11 |

To commence the method of the present invention, a bolus of such a mixture of analytical gases is inspired by the subject. See step 100 in FIG. 6. The inspired analytical gas mixture is carried by the breathing gases into the lungs of the subject where it participates in gas exchange with the blood. The amount of each analytical gas of the mixture that is absorbed into the pulmonary blood flow in a particular lung compartment (i) during the gas exchange depends on (1) the level of ventilation ($V_{ti}$) occurring in the compartment; (2) the volume ($V_{ti}+V_{ai}$) of the compartment; (3) the perfusion ($Q_i$) of the compartment; and (4) the solubility ($\lambda$) of the gas in the blood. Amounts of the analytical gases not absorbed into the blood remain in the breathing gases for expiration from the subject.

Figure 1:
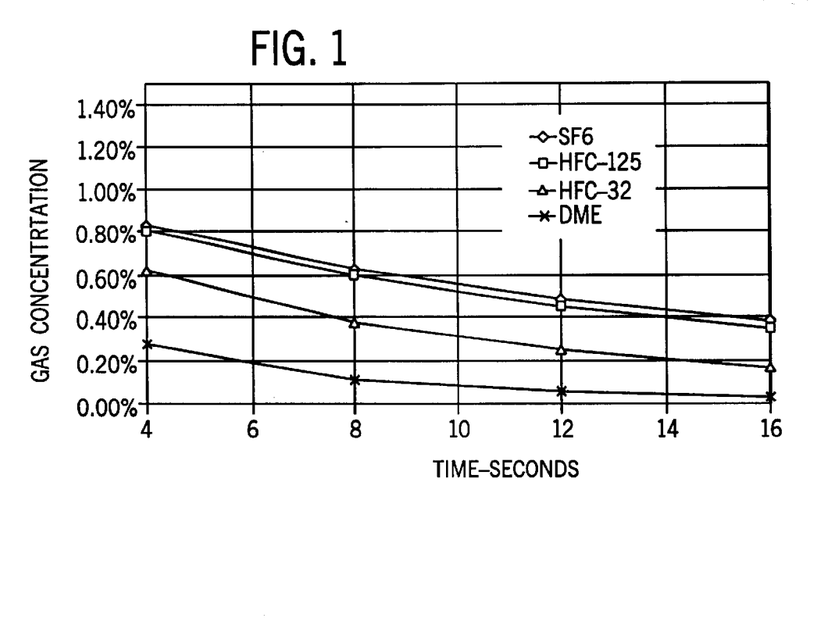
FIG. 1 is a graph showing one example of the concentrations of analytical gases measured in the expired breathing gases of a subject.

The concentration of each of the analytical gases is measured in the breathing gases expired by the subject. See step 102 in FIG. 6. FIG. 1 shows an example of gas concentration measurement for four expirations. The expirations are shown as occurring at equally spaced intervals of, for example four seconds, and the measurements are of end tidal gas concentrations in percentages. As noted below, the measurements can be performed for as long as no recirculation of the blood containing absorbed analytical gases occurs. This is typically 14–18 seconds for a subject at rest. The gas concentrations shown in FIG. 1 are representative of that which might be expected from a subject having generally normal, healthy lungs. The graphs are formed by connecting the sample points for each gas.

The following is to be noted in connection with FIG. 1. In general, the amount of a given analytical gas in the expired breathing gases is related to the solubility of the gas in the blood. For a gas, such as dimethyl ether (DME) having a high solubility in blood ($\lambda=11$), smaller amounts of the gas appear in the expired breathing gases than for a gas such as sulfur hexafluoride ($SF_6$) which has a low solubility ($\lambda=0.005$). The smaller amounts of expired dimethyl ether in the expired breathing gases are due to the greater uptake of this gas into the blood because of its high solubility. Less of the gas is found in the expired breathing gases. The greater amounts of expired sulfur hexafluoride are due to the smaller blood uptake of this gas because of its lower solubility. This results in more of the gas being expired.

The gas exchange characteristics of analytical gases of differing solubilities will also identify and categorize alveoli according to their V/Q ratio properties in a compartmental manner analogous to that described above in connection with the MIGET. For example, for an analytical gas of high solubility in blood, the gas will tend to go into the blood. The exception is compartments with low perfilsion. Thus such a gas categorizes the lung into compartments that have low perfusion (high V/Q ratio) and those that do not have low perfusion and the high V/Q ratio. Since the expired analytical gas is exhaled from compartments with low perfusion and a high V/Q ratio, a high solubility gas can be said to "see" low perflusion, high V/Q ratio compartments.

The opposite is true for an analytical gas with low solubility in blood. This gas will divide the lungs into compartments having high perfusion and those that do not have high perfusion. This gas will "see" high perfusion, low V/Q ratio compartments.

In the same manner, analytical gases with intermediate solubilities will compartmentalize the lungs at V/Q ratios intermediate the high and low V/Q ratios.

In addition to knowing the expired analytical gas concentrations, it is also possible to know the functional residual capacity (FRC) of the lungs. See step 104 in FIG. 6. As noted above, the functional residual capacity is the sum of the alveolar volumes $V_a$ of the compartments (i). The functional residual capacity can be measured by the gas wash-out method. This method is based on a determination of the amount of exhaled gas and corresponding changes in gas concentrations in the exhaled gas. In a basic form, the nitrogen in the air is used as a wash-out gas. The lung volume forming the functional residual capacity contains nitrogen in the same percentage as air, i.e. approximately 80%. The subject commences breathing pure oxygen. With each breath, nitrogen in the lungs is replaced by oxygen, or, stated conversely, the nitrogen is washed out of the lungs by the oxygen. The breathing of pure oxygen can continue until all the nitrogen is washed out of the lungs. By determining the volume of washed out nitrogen and knowing the initial concentration of nitrogen, the functional residual capacity can be computed.

It is also possible to use sulfur hexafluoride as the inert gas for function residual capacity measurement. See Jonmarker C. et al., Measurement of Functional Residual Capacity by Sulphur Hexafluoride Washout, Anesthesiology 1985, Vol. 63, No. 1: 89–95. Use of such a low solubility gas permits the measurements needed to determine functional residual capacity to be performed along with the measurements of expired analytical gas concentrations for purposes of determining compartmental tidal volume distribution. Because the solubility of sulfur hexafluoride is so low, measurements to determine functional residual capacity can continue even after recirculation of the blood since the blood contains little, if any, of this gas.

Another technique for determining functional residual capacity and in which sulfur hexafluoride may be used is described in U.S. patent application Ser. No. 09/240,722, filed Jan. 29, 1999 by Erkki Heinonen and assigned to a common assignee.

The method of the present invention employs expired gas concentration measurements of the type shown in FIG. 1. It may also employ the functional residual capacity of the lungs and/or the pulmonary blood flow (Q), if the latter is known.

Figure 2:
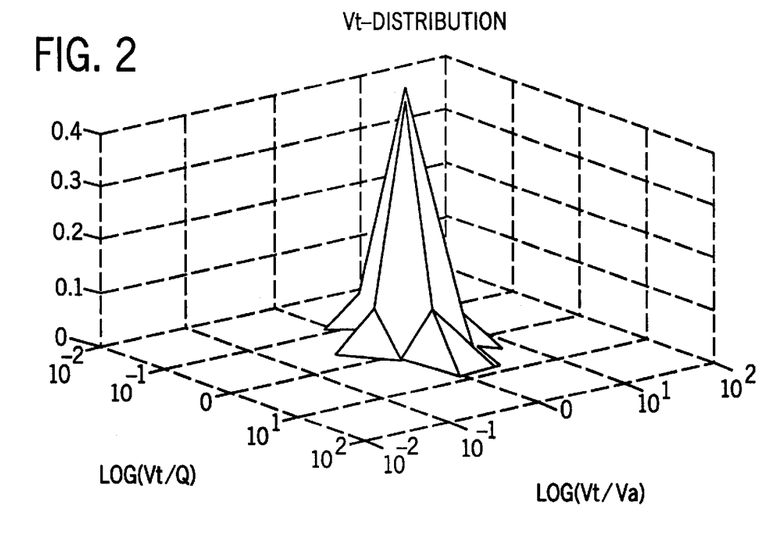
FIG. 2 is a graph showing diagnostic data corresponding to the breathing gas concentration measurements of FIG. 1.

The determination of compartmental tidal volume distribution carried out in the manner described in detail below, can be used to produce a graphic representation of the type shown in FIG. 2. The graph of FIG. 2 is produced from the gas concentration measurements shown in FIG. 1, which, as noted above, are representative of those that would be obtained from a subject having normal, healthy lungs. FIG. 2 contains a set of orthogonal axes in which the X and Y axes form a horizontal plane and the Z axis is vertical. The X axis is a logarithmic scale of the ventilation/perfusion ratio ($V_t/Q$). The Y axis is a logarithmic scale of the ventilation/gas volume ratio ($V_t/V_a$). The vertical Z axis, or ordinate, is a linear scale of the tidal volume ($V_t$) in some convenient units.

A $V_t/Q$ ratio and $V_t/V_a$ ratio coordinate is established in the X-Y plane for each compartment used in the determination. From the determination, the Z axis value, or $V_t$ value, for each coordinate is obtained from the mathematical derivation. An orthogonal X, Y, Z plot is thus made to produce the showing of FIG. 2.

From FIG. 2, it can be seen that most of the tidal volume $V_t$ is clustered in the center of X-Y plane meaning that the $V_t/Q$ and $V_t/V_a$ ratios for these compartments are neither excessively high or excessively low. Lesser tidal volume is found in higher or lower $V_t/Q$ and $V_t/V_a$ ranges. The showing of FIG. 2 indicates that both normal $V_t/Q$ ratios and $V_t/V_a$ ratios predominate in the lungs of the subject and that adequate oxygenation is occurring since most of the tidal volume $V_t$ is at locations where the $V_t/Q$ and $V_t/V_a$ ratios are normal.

Figure 3:
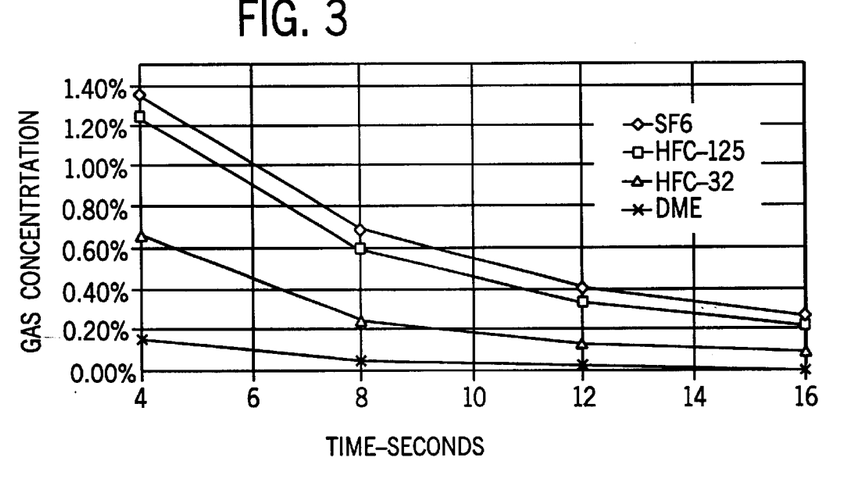
FIG. 3 is a graph, similar to FIG. 1, showing another example of analytical gases concentration measurements in the expired breathing gases of a subject.
Figure 4:
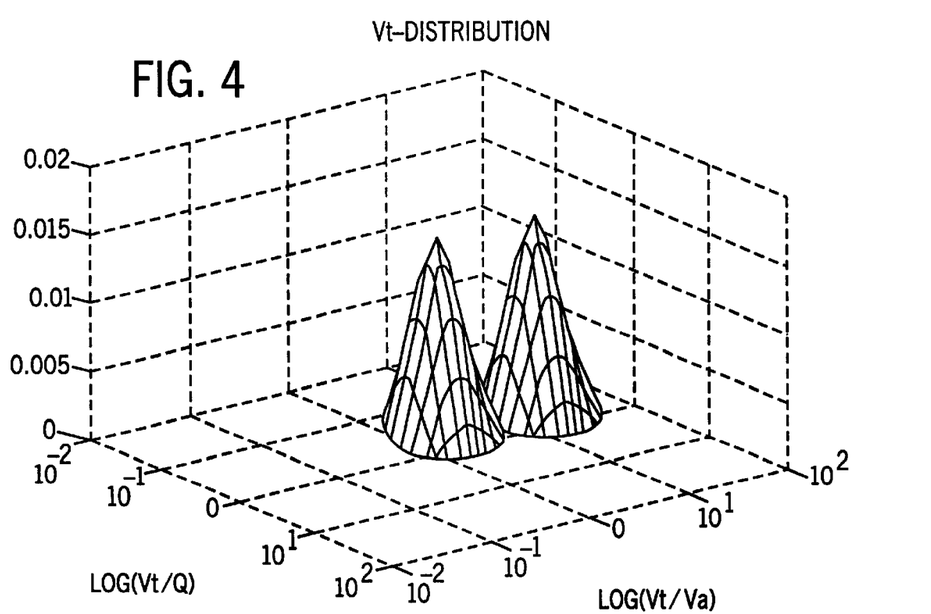
FIG. 4 is a graph, similar to FIG. 2, showing diagnostic data corresponding to the breathing gas concentration measurements of FIG. 3.

FIG. 3 shows expired analytical gas concentration measurements representative of those that might be obtained from a subject, whose lungs are abnormal, although the measurements are not those of any particular lung abnormality. The graphic display of FIG. 4 is produced from this data. The differences between the graphic display of FIG. 2 and that of FIG. 4 are readily apparent, particularly with respect to the inhomogeneous distribution of the tidal volume $V_t$ along the $V_t/V_a$ axis. The total tidal volume $V_t$ remains unchanged and the $V_t/Q$ ratio remains generally homogeneous in this example. Data of the type shown in FIGS. 2 and 4 can be used by a clinician to diagnose the presence and nature of lung abnormalities, undertake the appropriate treatment, and monitor the course of the therapy.

FIGS. 2 and 4 show the distribution of the tidal volume $V_t$ among compartments having known, assigned $V_t/Q$ and $V_t/V_a$ ratios. The method of the present invention can also be used in an analytical framework in which all compartments are assumed to receive the same tidal volume $V_{ti}$ and the distribution of these ratios among the compartments is determined. Or, it may be assumed that the compartments all have the same alveolar volume $V_{ai}$ and the distribution of the ventilation and perfusion among the compartments is determined. Or, it may be assumed that the compartments all have the same perfusion Q and the compartmental tidal volume and alveolar volume distributions are determined.

The method of the present invention is described, in detail, below as determining the compartmental distribution of tidal volume $V_t$.

To simplify the method of the present invention as well as to simplify the following explanation of the invention, the following assumptions are made or parameters established. Anatomical dead space in a subject's airways is neglected. For actual measurements, such dead spaces must be taken into account in the manner described below. The functional residual capacity FRC of the lungs is considered to be formed of parallel compartments (i). While, as noted above, the concept of "compartments" is largely an analytical one for use in the mathematical modeling of the lung, consideration of them as being in parallel roughly corresponds to the anatomy of the lung. The division of the lungs into compartments is deemed made in such a way that the concentrations of gases within each of the compartments are homogeneous. Certain other simplifying assumptions are noted below.

The concentration (F) of the inspired analytical gas mixture in the breathing gases of the subject is the volume of the bolus divided by the tidal volume of the subject or $$F_{insp} = V_{bolus}/V_T \tag{1}$$

where $F_{insp}$ is the inspired concentration, $V_{bolus}$ is the volume of the bolus and $V_T$ is the tidal volume. The analytical gas mixture bolus is distributed in the various compartments ($V_{ai}$) of the lungs in accordance with the ventilation ($V_{ti}$) of each compartment.

The concentration ($F_i$) of the analytical gas mixture in a given compartment may differ from that in other compartments due to inhomogeneous distribution of the inspired tidal volume $V_t$ among the compartments. The concentration of the analytical gas mixture in a given compartment (i) is $$F_i = V_{bolus} V_{ti}/(V_{ai} + V_{ti}) \tag{2}$$

The concentration of analytical gases expired by the subject will be equal to $$F_{exp} = (1/V_t)\Sigma_i V_{ti} F_i = (V_{bolus}/V_t^2)\Sigma_i (V_{ti})^2/(V_{ai}+V_{ti}) \tag{3}$$

Since the inspired analytical gases employed in the method of the present invention are soluble to a greater or lesser extent in the blood of the subject, the expired concentration of the gas will be less than that determined by Equation (3) by the amount that participates in gas exchange from the breathing gases to the blood in the capillary field and is thus absorbed into the blood. As noted above, the amount of a given analytical gas absorbed in the pulmonary blood flow in a particular lung compartment depends on the ventilation, the alveolar volume, and the perfusion of the compartment, and the solubility of the gas in the blood. For each compartment, the absorption of a given analytical gas into the pulmonary blood flow can be computed from Fick's law as $$d(F_i(V_{ai}+V_{ti}))/dt = -\lambda Q_i(F_i^{art} - F_i^{ven}) \tag{4}$$

where $\lambda$ is the blood/gas partition coefficient of the gas, $Q_i$ is the magnitude of perfusion of the compartment (i), and $F_i^{art}$ and $F_i^{ven}$ are the concentrations of the analytical gas expressed as corresponding arterial and venous partial pressures. If a particular analytical gas does not exist in the body of the subject before performing the method of the present invention, the venous partial pressure is zero, up to the time recirculation of blood in the body occurs.

Also, some amount of soluble analytical gases will be absorbed into the pulmonary tissue of the lung and into water in the lung. For simplicity, these effects are omitted in the present description. They will be discussed, in detail, later when the method is extended to the measurement of the pulmonary tissue and lung water volume.

Figure 5A:
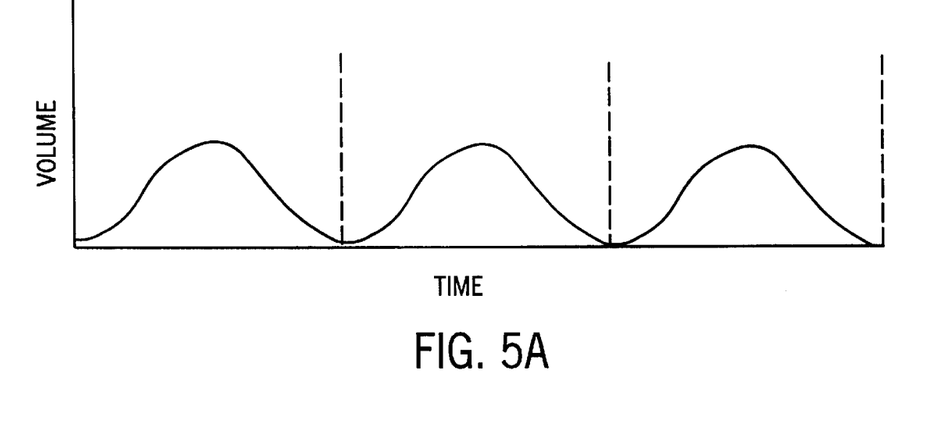
FIG. 5A shows a typical breathing gas volume with respect to time graph for a subject.
Figure 5B:
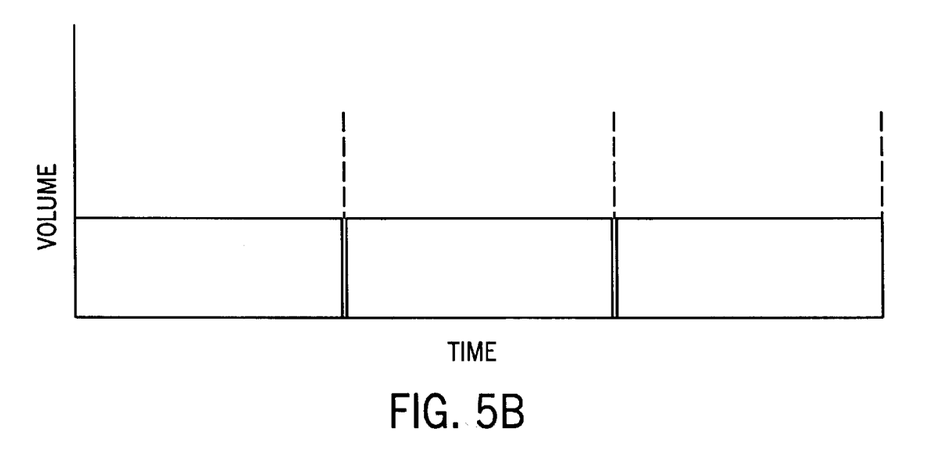
FIG. 5B shows, in graphic form, a simplifying assumption for the breathing gas volume with respect to time used to facilitate the explanation of the present invention.

Since as noted in Equation (4), analytical gas absorption is dependent on time, to facilitate the following explanation, a simplified breathing pattern of expiration and inspiration is used. A typical graph of breathing gas volume with respect to time for normal breathing is shown by the graph of FIG. 5A with volume on the ordinate and time on the abscissa. In the following explanation, it is assumed that both expiration and inspiration take place instantaneously and inspiration takes place immediately after the preceding expiration. The durations $\Delta t$ and tidal volumes of all breaths are considered equal. A graph of such a breathing pattern having volume on the ordinate and time on the abscissa would resemble the sequence of square waves shown in FIG. 5B. Modification of the equations employed in the explanation to the actual situation occurring in the lungs of the subject is straightforward but would make the equations used in the explanation below, unnecessarily cumbersome.

With the foregoing assumptions, the volume $(V_{ai}+V_{ti})=V_i$ of the individual alveolar compartment becomes independent of time. The time related behavior of the analytical gas concentration $F_i$ in a compartment is given by $$F_i(t) = F_{io}\exp(-\lambda(Q_i/V_i)t) \tag{5}$$

where t is the time after inspiration and $F_{io}$ is the initial concentration. The remaining concentration of a given gas in a particular individual compartment (i) thus depends on the solubility of that gas in the blood and on the ratio $(V_i/Q_i)$.

While Equation (5) gives the concentration of the analytical gases in the lung compartments, what is available for measurement are the breathing gases expired by the subject in each breath. The expired end tidal concentration at the end of the first breath for each gas is $$F_{exp} = (1/V_t)\Sigma_i V_{ti} F_i = (V_{bolus}/(V_t^2))\Sigma_i(V_{ti})^2/(V_{ai}+V_{ti})\exp(-\lambda Q_i \Delta t/(V_{ai}+V_{ti})) \tag{6}$$

where $\Delta t$ is the duration of the breath. Subsequent inspirations, which contain no additional bolus gas, further dilute the compartmental concentrations ($F_i$). The expired concentration $F_{exp}$ ($\lambda$,n) after breath n for each gas is then $$F_{exp}(\lambda,n) = (V_{bolus}/V_t^2)\Sigma_i((V_{ti})^2 V_{ai})(V_{ai}/(V_{ai}+V_{ti}))^n \exp(-\lambda Q_i n \Delta t/(V_{ai}+V_{ti})) \tag{7}$$

Figure 6:
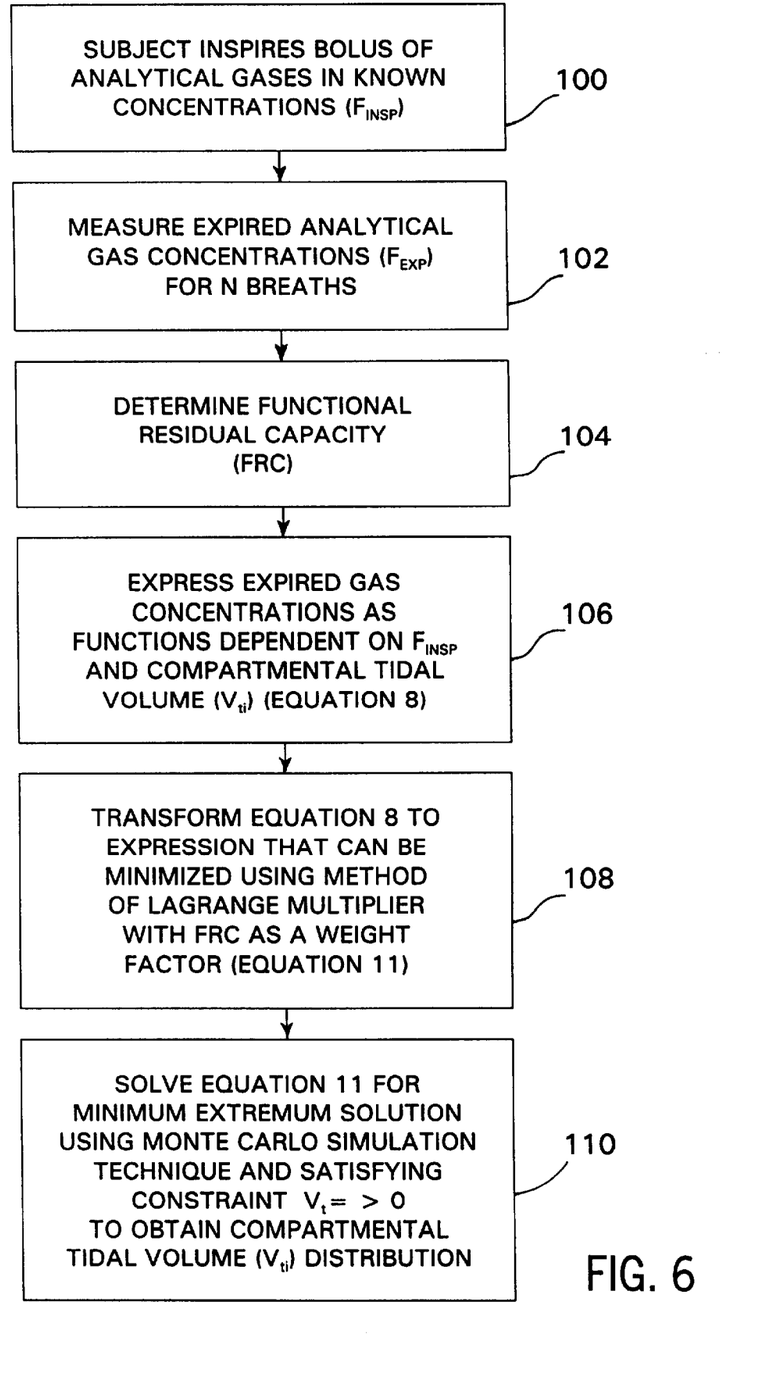
FIG. 6 is a flow chart describing the method of the present invention.

In step 106, Equation (7) can be rewritten in terms of the ventilation/volume-ratio $V_{ti}/V_{ai}=x_i$ and the ventilation/perfusion-ratio $V_{ti}/Q_i=y_i$ as follows:

$$F_{exp}(\lambda,n) = (V_{bolus}/V_t^2)\Sigma_i V_{ti} g(x_i,y_i,\lambda,n) \tag{8}$$

where $$g(x_i,y_i,\lambda,n) = x_i/(x_i+1)^n \exp(-\lambda x_i n \Delta t/(y_i(x_i+1))) \tag{9}$$

In the present example, there will be sixteen Equations (8), i.e. four analytical gases of differing solubilities and four breaths. It now becomes necessary to determine the values of $V_{ti}$.

An arbitrary discrete set of values $(x_i,y_i)$ can be used to represent the possible compartments of the analytical model.

A sufficiently general representation is obtained, for example, by letting both $x_i$ and $y_i$ independently range from 0.01 to 100 in $N_{dist}$=20 equidistant steps on a logarithmic scale. This results in $N_{dist}*N_{dist}$=400 compartments (i), each of which has a specified ventilation/volume ratio $x_i$ and ventilation/perfusion ratio $y_i$.

Equation (8) can be written as a matrix equation $$f = A \cdot v \tag{10}$$

Column vector f contains the $N_{breaths}*N_{gases}$ measured values $f(\lambda,n)=(V_t/F_{insp})F_{exp}(\lambda,n)$ where $N_{breaths}$ is the number of breaths and $N_{gases}$ the number of gases used. The matrix A with dimensions $(N_{breaths}*N_{gases}*N_{dist}*N_{dist})$ consists of the computed values $g(x_i,y_i,\lambda,n)$. (The asterisk sign connotes multiplication.) The column vector v contains the $N_{dist}*N_{dist}$ compartmental ventilations $V_{ti}(x_i,y_i)$ to be solved.

In Table 2 the above formalism is compared with that of the MIGET. MIGET is a static measurement with no concepts such as time or breath; one measured value is obtained for retention and excretion of each gas so that the dimension of the corresponding vector f is $2*N_{gases}$. In the MIGET only the ratios $V_{ti}/Q_i=y_i$ are considered, so that the dimension of the corresponding vector v is $N_{dist}$. The form of the function $g(x_i,y_i,\lambda,n) \rightarrow g(y_i,\lambda)$ is quite different due to the different dynamics of the steady state constant venous infusion compared to the inspiratory bolus gases dilution and their absorption into the blood.

TABLE 2

|  | This method | MIGET |
| --- | --- | --- |
| Dimension of vector f | $N_{breaths}*N_{gases}$ | $2*N_{gases}$ |
| Dimension of matrix A | $N_{breaths}*N_{gases}*N_{dist}*N_{dist}$ | $2*N_{gases}*N_{dist}$ |
| Dimension of vector v | $N_{dist}*N_{dist}$ | $N_{dist}$ |
| Function g | $x_i/(x_i + 1)^n \exp(-\lambda x_i n \Delta t/(y_i(x_i + 1)))$ | $\lambda \Delta t/\lambda(\Delta t + y_i)$ |

Knowing the functional residual capacity (FRC), obtained as described above, permits the solution of the compartmental ventilation distribution by the Lagrange multiplier technique. In step 108, Equation (10) is transformed to an optimization problem in which the expression to be minimized is:

$$E = [f - A \cdot v]^2 + w_{FRC}(FRC - \Sigma_i(V_{ti}/x_i))^2 \tag{11}$$

where $w_{FRC}$ is a weight factor (Lagrange multiplier) to be chosen.

It is also possible that other variables are either known or unknown. If functional residual capacity (FRC) and perfusion (Q) are both known, the equation becomes:

$$E = [f - A \cdot v]^2 + w_{FRC}(FRC - \Sigma_i(V_{ti}/x_i))^2 + w_Q(Q - \Sigma_i(V_{ti}/y_i))^2 \tag{12}$$

If only perfusion (Q) is known, then the equation is:

$$E = [f - A \cdot v]^2 + w_Q(Q - \Sigma_i(V_{ti}/y_i))^2 \tag{13}$$

If neither FRC nor Q is known, the equation is:

$$E = [f - A \cdot v]^2 \tag{14}$$

Thus, there are four possible functions that can be minimized. However, because FRC is relatively easy to obtain, the likeliest case which arises is when FRC is known, and the following example will be given using Equation 11.

The task is now to find the distribution of compartmental tidal volumes $V_{ti}$ which minimize E and satisfy the constraint $V_{ti}>=0$. The constraint reflects that it is anatomically correct and in accordance with the physiological functioning of the subject's lungs to say that the compartment tidal volume ($V_t$) of the subject should be non-negative.

In the method of the present invention, a Monte Carlo simulation technique is applied in step 110. The term "Monte Carlo technique" or "Monte Carlo method" describes techniques by which problems involving a complex system, such as those arising out of chemistry, physics, geology, economics, etc. can be investigated. While the method comprises numerous subsets directed to specific applications, an essential characteristic of the Monte Carlo method is the use of random sampling techniques to arrive at a solution to the physical, or other, problem. The Monte Carlo simulation technique is described in *Introductory Statistics*, T. H. Wonnacott and R. J. Wonnacott, John Wiley & Sons, 5th Ed. 1990, pages 218–225, as well as at Internet locations such as "http//www.npac.syr.edu/users/paule/lectures/montecarlo/p_montecarlo.html" and "http//csepl.phy.oml.gov/mc/node1.html". As noted in the above textual reference, a digital computer lends itself to the reiterative computations typically utilized in a Monte Carlo simulation.

The Monte Carlo technique can be employed to find values of compartmental tidal volumes $V_{ti}$, i.e. the compartmental ventilation distribution, that minimize the value of E within the constraints noted above. To this end, the compartmental tidal volume distributions are modeled by a physical system: the compartmental volumes $V_{ti}$ are interpreted as the "degrees of freedom" of the system, and the function E to be minimized is interpreted as an "energy" E of the system. The Monte Carlo simulation procedure sequentially generates ventilation distributions $V_{ti}$, in which a particular distribution appears with a probably given by the Maxwell-Boltzmann distribution function, $P_{MB}(E)=\exp(-E/T)$, where T is the "temperature" of the system. When T=0, the probability of the ventilation distribution which corresponds to the minimum value of energy E=0 is equal to one, and the probability of all distributions with E>0 is equal to zero. When T>0, distributions with E>0 appear with finite probability. Simulation at higher temperatures thus allows for the distribution to change so that it can move from one minimum solution to another minimum.

The simulation uses the analytical gas concentrations expired by the subject, such as those shown in FIG. 3. For descriptive purposes, the values of FIG. 3 may be deemed to be those that characterize unhealthy lungs. The lungs may be deemed ventilated with 8000 ml/min of breathing gases at a respiration rate of 15 breaths/minute, i.e. one breath every four seconds as shown in FIG. 3. A bolus of the four analytical gases of Table 1 is mixed in the inspiratory gases of a single breath to provide an inspiratory concentration of 4.0% for each gas. The expired concentrations of the first breath are on the order of 1%.

The initial compartmental ventilation distribution can be chosen arbitrarily. In the present example, an initial compartmental ventilation distribution corresponding to that deemed to be present in healthy lungs is used. This distribution is graphically shown in FIG. 2 as a unimodal Gaussian ventilation distribution. The expired concentrations $F_{exp}(\lambda,n)$ used to obtain the ventilation distribution shown in FIG. 2 are shown in FIG. 1. An initial FRC value of 2500 ml is used in the simulation. The simulation is started at a relatively high temperature. In general, a given value for E will result by applying to Equation (11), the actual expired concentrations shown in FIG. 3, the initial compartmental ventilation distributions $V_{ti}$ shown in FIG. 2, and the initial FRC value.

Since the overall tidal volume $V_T$ of the subject does not change, the compartmental ventilation change in the simulation continuation is one in which an increment of tidal volume is taken from one randomly selected compartment and added to another randomly selected compartment. The corresponding energy change, $\Delta E$, is then calculated.

If the $\Delta E$ is negative, the incremental variation in the volume distribution is accepted. If the $\Delta E$ is positive, the probability that the change in ventilation distribution is accepted depends upon the Maxwell-Boltzmann distribution function. In this simulation, the Maxwell-Boltzmann distribution function P is:

$$P = \exp(-\Delta E/T) \qquad (15)$$

The quantity P is then subtracted from 1 to obtain a value X:

$$X = 1 - P \qquad (16)$$

Suppose 0<Y<1 is a number selected by a random number generator. If X>Y, the solution is discarded. If X=<Y, the solution is accepted. It is noted that when T=0, then X=1, and the solution is never accepted since X is always greater than Y. Alternatively, when T is a high value, then P approaches 1 and X approaches zero. When X=0, the solution is always less than the randomly generated value Y, and the solution is always accepted.

The iterative process is performed at two temperatures, T>>0 and T=0, for further incremental changes using different randomly selected compartments until a compartmental ventilation distribution that minimizes the expression E is arrived at.

Figure 7:
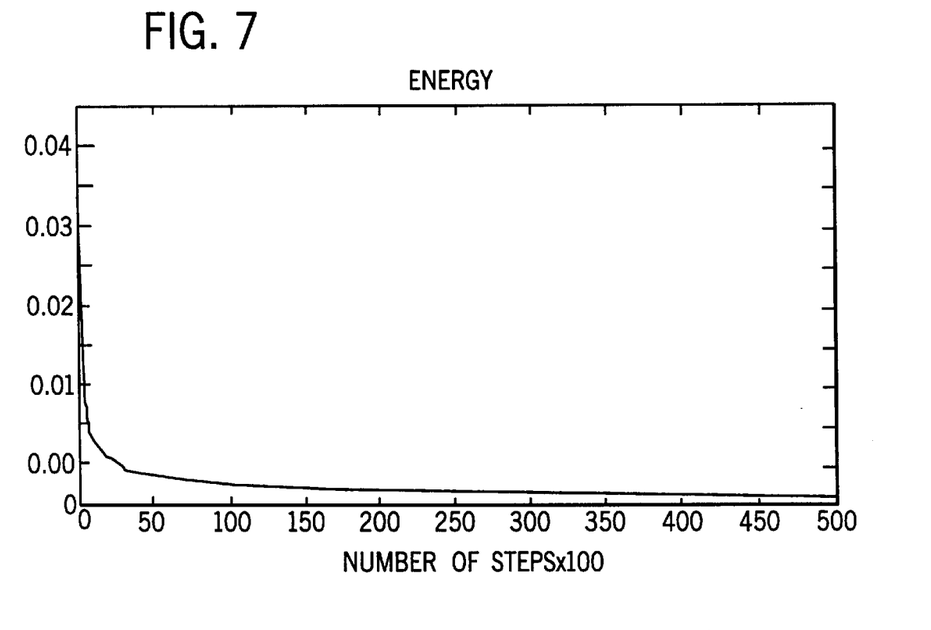
FIG. 7 shows the convergent behavior of the mathematical analysis used in the method of the present invention as it relates to energy.

The process is graphically seen in FIG. 7 in which the minimization of the ordinate value of E from a determination of a compartmental tidal volume ventilation $V_{ti}$ distribution through 50,000 iterations of the latter is shown. An example of a compartmental ventilation distribution that may result for the unhealthy lungs is graphically shown in FIG. 4. The bi-modal distribution of FIG. 4 clearly differs from the unimodal distribution of healthy lungs shown in FIG. 2.

The solution that is obtained at T=0 may be either a global minimum, or a local minimum. Repeating the procedure some number of times at T>>0 and T=0, the distribution corresponding to the lowest value of E can be found. At T>>0, the distribution can wander from an initial state randomly to find various minimum value solutions. This way, all the minimums can eventually be found.

The resulting distribution may not be a single unique result. There may be several distributions which have almost the same overall gas exchange properties. In this case, one solution can be interpreted as a representation of the class of distributions.

Simulations of the method of the present invention show that a random experimental error in the absolute concentrations of at least 0.01% can be tolerated. This corresponds to the order of accuracy currently obtainable in infrared measurements of, for example, $SF_6$ and $N_2O$. If the system is properly calibrated there should not be any relevant systemic errors in the mathematical determination.

The solution described above can also be used to determine pulmonary blood flow Q in the following manner. In creating the analytical compartments, a ventilation/volume ratio for each compartment is established on one axis and a ventilation/perfusion ratio is established on the other axis of the orthogonal axes system of FIGS. 2 and 4. Hence the ventilation/perfusion ratio in each compartment is a known quantity. The tidal ventilation $V_{ti}$ for each compartment is determined by the Monte Carlo simulation previously described. By applying the value of the tidal ventilation $V_{ti}$, so determined, for a given compartment to the ventilation/perfusion ratio for the compartment, the compartmental perfusion $Q_i$ can be obtained. The pulmonary blood flow Q is the sum of the pulmonary perfusion for all compartments.

Figure 8:
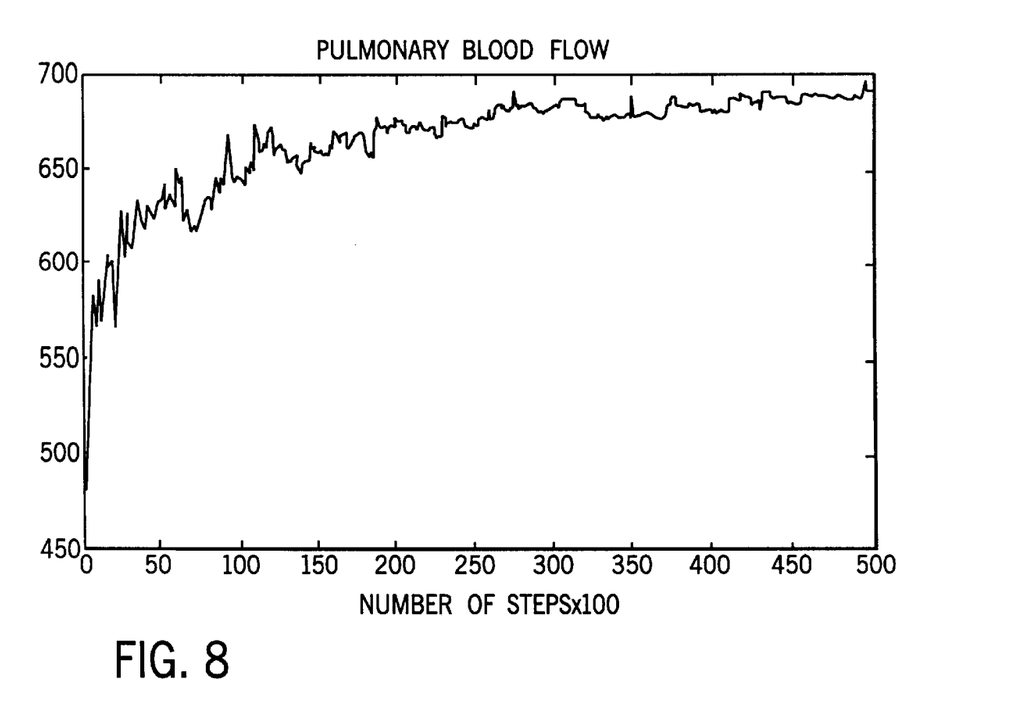
FIG. 8 shows the convergent behavior of the mathematical analysis used in the method of the present invention as it relates to pulmonary blood flow.

FIG. 8 shows how the pulmonary blood flow Q develops with the iterations of the Monte Carlo simulation. The value for pulmonary blood flow Q used at the beginning of the process is that which corresponds to the initial compartmental ventilation distribution. In the example used herein, this is 5000 ml/min. As the compartmental ventilation distribution changes in the course of the Monte Carlo simulation technique to arrive at a distribution that minimizes the expression E, the value of pulmonary blood flow correspondingly changes to arrive at a final value, which in the case of FIG. 6 is approximately 700 ml/min.

Starting from the combined "two-dimensional" $V_t/Q$ and $V_t/V_a$ distribution obtained by the present method, it is possible to obtain a "one-dimensional" $V_t/Q$ distribution such as those given by MIGET. This is done by combining the compartments with the same $V_t/Q$ ratio different $V_t/V_a$ ratios into one compartment and adding the corresponding tidal volumes together. Similarly, one could compute a "one-dimensional" $V_t/V_a$ distribution by combining compartments with the same $V_t/V_a$ ratio but different $V_t/Q$ ratios into one compartment.

The method of the present invention has been described, above, in an embodiment in which both the ventilation/perfusion ($V_t/Q$) ratio on the X axis and the ventilation/volume ($V_t/V_a$) ratio on the Y axis extend over a range of values. However, the method can also be practiced in a form in which one or the other of the ventilation/perfusion ratio or the ventilation/volume ratio is established at a fixed value. The data provided by the method, and the resulting graphic display, would then be two dimensional, rather than three dimensional as shown in FIGS. 2 and 4.

The method of the present invention has been described, above, in an embodiment in which the ventilation/perfusion and ventilation/volume ratios are established and Equation (8) is solved for the compartmental tidal volume ($V_{ti}$) distribution. The choice of the values of the ventilation/perfusion and ventilation/volume ratios which span the X and Y axes fixes the particular division of the lung into compartments. This formulation is not, however, the only possibility. One has considerable freedom in choosing the principle by which the lung is divided. One might, for example, divide the total tidal volume ($V_t$) into equal unit volumes ($V_{ti}$) of, for example, one cubic centimeter each, in which case the solution would provide the compartmental volumes ($V_{ai}$) seen by these unit volumes. In this formulation, one would apply Equation (8) to solve how large a portion of the lung volume (FRC) a given unit of tidal volume sees and how large a portion of the total perfusion (Q) it sees. Or, it would be possible to divide the lung volume (FRC) into equal units of compartmental volumes ($V_{ai}$) and solve Equation (8) to learn how much of the tidal volume ($V_t$) a particular compartment receives and how much of the perfusion (Q) is present in a particular compartment. All these kinds of alternative formulations would provide essentially the same information. The advantage of the approach described in detail, above, in which the compartmental tidal volumes ($V_{ti}$) are chosen as the variables to be solved is that the Equation (8) is linear with respect to ($V_{ti}$) which makes the treatment of the problem more straightforward mathematically.

While the method of the present invention has the numerous advantages described above, it will be appreciated that measurements are made only on the ventilatory side of the gas exchange system. Information of the perfusion side of the gas exchange system is obtained indirectly from the mathematical analysis. For this reason, the accuracy of the method to detect compartments with very small amounts of ventilation with respect to perfusion is reduced over that obtainable with the MIGET in which measurements are taken directly on the perfusion side. However, because of the reduced ventilation, these compartments play only a negligible role in oxygenation. And, the method of the present invention is simple and quick compared with the MIGET.

Also, with the method of the present invention, for most gases the measurements can only be performed as long as no recirculation of blood containing absorbed analytical gases takes place. For these gases, the time window is about 14–18 seconds for a patient at rest. For some gases, which are insoluble in the blood, or where the solubility in tissue is significantly greater than the solubility in blood, more time can be allowed to lapse. Thus, more breaths could be used in the measurement. Compartments which are not reached during the sampling time are allocated as zero ventilation. However, these compartments are also insignificant with respect to oxygenation. In either of the foregoing circumstances, if ventilation is improved, as by clinical intervention, it will be observed as soon as it becomes effective within the available time window.

When analytical gases with very high solubilities are inspired, a substantial portion of the gas is dissolved in the mucosa of the airways during inspiration and evaporates during expiration. It thus does not reach the lungs of the subject. But, as the method of the present invention will typically be used for intubated patients, this restriction may be minimal from the practical standpoint. However, for the foregoing reasons, it may be advisable not to use gases with blood/gas partition coefficients much higher than 10. This would mean that compartments which have ($V_t/Q$)$_i$ ratios higher than about 50 times the normal value would be interpreted as a single poorly perfused compartment. This is obviously not a serious limitation for the applicability of the method.

As noted above, the method of the present may additionally be used to determine the amount of volume of pulmonary tissue and the amount of lung water (edema) in the lungs. In this connection, it should be noted that the tissue solubility properties of analytical gases such as those discussed above, resemble the solubility properties in blood. That is, a gas with low solubility in blood will exhibit low solubility in tissue and water and a gas with high solubility in blood will exhibit high solubility in tissue and water. For simplicity, it is assumed that the blood/gas, tissue/gas, and water/gas partition coefficients of the high solubility gas are all equal and are denoted by $\lambda$. Using an insoluble gas, such as helium, i.e. $\lambda$ is zero, or a gas of low solubility, such as sulfur hexafluoride, the functional residual capacity of the subject's lungs can be determined. When a gas of high solubility, such as dimethyl ether, is used the amount $\lambda$ $V_{tissue}$ will be taken up by pulmonary tissue volume $V_{tissue}$ and the amount $\lambda$ $V_{water}$ will be taken up by the lung water volume $V_{water}$. The "effective FRC" seen by the high solubility gas then corresponds to $FRC^{eff}=FRC+\lambda(V_{tissue}+V_{water})$. Knowing the actual FRC, the sum of tissue volume and lung volume water can be determined. This may comprise useful diagnostic information. If it is desired to obtain the amount of water in the lung, this may be obtained by estimating the amount of lung tissue from known data based on age, sex, body build, height, and weight and subtracting same from the sum of lung tissue and water volume. Such techniques are described in Overland, E. S. et al., Measurement of pulmonary tissue volume and blood flow in persons with normal and edematous lungs, J. Appl. Physiol. 1981; 51(6): 1375–1383. However, in the conventional technique, the lungs are assumed to be homogeneous in nature so that they comprise one compartment. In situations in which the lungs are inhomogeneous, this assumption will lead to inaccurate results.

Since the method of the present invention takes into account possible inhomogeneous distribution of ventilation with respect to lung volume and perfusion, it provides a more accurate determination of the lung tissue volume and the amount of lung water. The compartmental volumes $V_{ai}$ seen by the high solubility gas and low solubility gas differ from each other by $\lambda(V_{tissue,i}+V_{water,i})$, where $V_{tissue,i}$ corresponds to the pulmonary tissue volume and $V_{water,i}$ to the lung water volume associated with the compartments (i). The sum of these volumes may be denoted as $V_{li}=V_{tissue,i}+V_{water,i}$ and the total sum $V_l=\Sigma_i V_{li}=V_{tissue}+V_{water}$. The effective compartmental volume seen by the high solubility gas corresponding to compartment (i) is then $V_{ai}^{eff}=V_{ai}+\lambda V_{li}$.

In order to include the effect of pulmonary tissue volume and lung water in Equations (8) through (14), the compartmental volume $V_{ai}$ should be replaced by the effective compartmental volume $V_{ai}^{eff}=V_{ai}+\lambda V_{li}$. This formulation would introduce $N_{dist}*N_{dist}$ additional unknown variables $V_{li}$ to be solved. The number of unknowns can be reduced, however, by applying additional constraints derived from physiology. For example, one may normally assume that the lung tissue is approximately homogeneously distributed with respect to alveolar volume. Then $V_{li}/V_{ai}=V_l/FRC$ so that $V_{ai}^{eff}=V_{ai}+\lambda(V_l/FRC)V_{ai}=(1+(\lambda V_l)/FRC)V_{ai}$. In this case, only one additional unknown, $V_l$, is introduced. This can be solved for by the Monte Carlo method together with the tidal volume distribution $V_{ti}$.

If there is a substantial amount of water (edema) located in a restricted part of the lung, the assumption of homogeneous distribution of $V_{li}$ with respect to alveolar volume would not be valid. In this case, the energy value E of the Monte Carlo simulation procedure would fail to converge to a value close to zero. Since edema is associated with a significant diffusion impairment, one can in this case apply a constraint which associates the lung water with those parts of the lung that correspond to deadspace with $Q_i=0$.

As noted above, it is necessary to correct the determination described above for anatomical dead spaces in the lungs of the subject. During the first breath taken by the subject, fresh breathing gases containing the bolus of analytical gases will be inspired by the subject through the airway passage that commences with the mouth, nose, or trachea of the subject and ends in the alveoli. The bolus can be administered early in the inspiration to ensure that the lungs are filled with breathing gases containing the analytical gases. On expiration, breathing gases are discharged from the lungs of the subject. A portion of the breathing gases pass out of the subject. These are the gases used to measure the exhaled concentration of analytical gases. A portion of the breathing gases with which the analytical gases are mixed comes to reside in anatomical dead spaces, such as the trachea and bronchi of the airway and are not discharged.

This portion of the breathing gases may amount to 30% of the tidal volume of the subject.

In subsequent breaths by the subject, the breathing gases in the dead space will re-enter the subject's lungs. In the subsequent breaths, a quantity of fresh gases that do not contain the analytical gases are also inspired into the lungs of the subject. It is these fresh gases that further dilute, or reduce the concentration of, the analytical gases. Therefore, to provide correct concentration values, the dead space volume of the airway passage is subtracted from the tidal volume to determine the amount of diluent fresh breathing gases supplied to the lungs. The amount of the dead space volume can be determined by measuring the flow of the breathing gases and monitoring the concentration of the expired analytical gases, when the concentration of analytical gases in the expired breathing gas begins to change, it is an indication that the expired gases are now coming from the lungs and not the dead spaces. Gas flow prior to this time can be integrated to determine the volume which came from the dead spaces.

Also, as noted above, to simplify the foregoing explanation, the volume $V_i$ of the individual alveolar compartments was considered to be independent of time. For the actual breathing of the subject, the volume of the individual alveolar compartments will vary as the subject expires and inspires as shown in FIG. 5A. Hence the alveolar volume, should be expressed in a form that is time dependent, for example, as $(V_{ai}+V_{ti}(t)=V_i(t))$ when used in the above equations.

It is recognized that other equivalents, alternatives, and modifications aside from those expressly stated, are possible and within the scope of the appended claims.

What is claimed is:

1. A method for determining the distribution of the tidal volume $(V_t)$ of gases inspired by a subject into his/her lungs, the distribution being among a plurality of compartments (i), each compartment having an assigned ratio value of a compartmental tidal volume $(V_{ti})$ to a compartmental perfusion $(Q_i)$ and an assigned ratio value of the compartmental tidal volume $(V_{ti})$ to a compartmental volume $(V_{ai})$ so that the compartments, collectively, cover at least one of a range of ventilation/perfusion ratio $(V_t/Q)$ values and a range of ventilation/volume $(V_t/V_a)$ ratio values, said method comprising the steps of:

(a) causing the subject to inspire a bolus of analytical gases in a tidal volume of breathing gases, the analytical gases of the bolus having differing solubilities in the blood of the subject and being inspired in known amounts;

(b) measuring the concentrations of the analytical gases in the breathing gases expired by the subject for at least one breath of the subject;

(c) expressing the expired concentrations of analytical gases in a form $$F_{exp}(\lambda,n)=(V_{bolus}/V_t^2)\Sigma_i V_{ti} g(x_i,y_i,\lambda,n) \quad (8)$$

where $$g(x_i,y_i,\lambda,n)=x_i/(x_i+1)^n \exp(-\lambda x_i n \Delta t/(y_i(x_i+1))) \quad (9)$$

wherein:
   $F_{exp}$=expired analytical gas concentration
   $V_{bolus}$=volume of analytical gas bolus
   $V_t$=tidal volume
   $V_{ti}$=compartmental tidal volume
   $V_{ai}$=compartmental alveolar volume
   $X_i$=compartmental ventilation/volume ratio, $V_{ti}/V_{ai}$
   $y_i$=compartmental ventilation/perfusion ratio, $V_{ti}/Q_i$
   $\lambda$=solubility
   n=breath number
   $\Delta t$=duration of breath (d) solving the expressions of step (c) to obtain a compartmental tidal volume $(V_{ti})$ distribution among the compartments that represents a solution to the expressions of step (c).

2. A method according to claim 1 further including the step of transforming the expressions of step (c) to a minimization/maximization problem in which an energy function E can be minimized or maximized and for which at least one extremum value may be obtained by application of an appropriate constraint.

3. A method according to claim 2 further defined as obtaining a minimum extremum value.

4. A method according to claim 2 wherein the step of solving the expressions of step (c) is further defined as obtaining a plurality of minimum extremum values.

5. A method according to claim 2 wherein the extremum solution corresponds to a distribution of the tidal volume $(V_t)$.

6. A method according to claim 3 wherein the minimum extremum solution corresponds to a distribution of the tidal volume $(V_t)$.

7. A method according to claim 2 wherein the solving of the expressions of step (c) is further defined as being carried out within the constraint that the tidal volume $(V_t)$ be equal to or greater than zero.

8. A method according to claim 6 wherein the solving of the expressions of step (c) is further defined as being carried out within the constraint that the tidal volume $(V_t)$ be equal to or greater than zero.

9. A method according to claim 2 wherein solving the expressions of step (c) further includes relating the expressions of step (c) to a selected probability density function.

10. A method according to claim 9 wherein the selected probability density function is a modified Maxwell-Boltzmann probability density function.

11. A method according to claim 9 wherein the probability density function is dependent on a temperature and a change in energy $(\Delta E)$.

12. The method according to claim 11 wherein solving the expressions of step (c) is further defined as transferring an incremental tidal volume from one randomly selected compartment to another randomly selected compartment to obtain an energy change $(\Delta E)$.

13. A method according to claim 12 wherein an energy change $(\Delta E)$ of one direction is accepted as a solution and the probability of the acceptance of an energy change $(\Delta E)$ of the other direction is dependent on the modified Maxwell-Boltzmann probability distribution function.

14. A method according to claim 12 wherein a negative energy change $(\Delta E)$ is accepted as a solution and the probability of the acceptance of a positive energy change $(\Delta E)$ is dependent on the modified Maxwell-Boltzmann probability distribution function.

15. A method according to claim 2 wherein the function E is minimized using the method of Lagrange multipliers.

16. A method according to claim 15 further including the step of ascertaining at least one of the functional residual capacity (FRC) of the lungs of the subject and the pulmonary blood flow (Q) of the subject and wherein a weight factor in the method of Lagrange multipliers relates to at least one of functional residual capacity and pulmonary blood flow.

17. A method according to claim 16 wherein the solution of the expressions of step (c) is solved using a Monte Carlo simulation.

18. A method according to claim 17 further including the step of ascertaining at least one of the functional residual capacity (FRC) of the lungs of the subject and the pulmonary blood flow (Q) of the subject and wherein a weight factor in the method of Lagrange multipliers relates to at least one of the functional residual capacity and pulmonary blood flow.

19. The method according to claim 17 wherein the solution using the Monte Carlo simulation commences with a tidal volume distribution deemed to be present in healthy lungs.

20. A method according to claim 1 wherein $x_i$ is a constant and wherein the compartments occupy a range of ventilation/perfusion ratio ($V_t/Q$) values.

21. A method according to claim 1 wherein $y_i$ is a constant and wherein the compartments occupy a range of ventilation/volume ratio ($V_t/V_a$) values.

22. A method according to claim 1 wherein $x_i$ and $y_i$ are variables and wherein the compartments occupy a range of ventilation/perfusion ratio ($V_t/Q$) values and a range of ventilation/volume ratio ($V_t/V_a$) values.

23. A method according to claim 1 wherein step (a) is further defined as causing the subject to inspire analytical gases having solubilities in a desired range of solubilities.

24. A method according to claim 1 wherein step (a) is further defined as causing the subject to inspire analytical gases having solubilities ($\lambda$) ranging from 0.05 to greater than 10.

25. A method according to claim 1 wherein step (a) is further defined as causing the subject to inspire analytical gases selected from $SF_6$; NO; $N_2O$; $(CH_3)_2O$; $CH_3OCH$; $CH_2$; $CO_2$ and fluorated hydrocarbons (HFC) 125, 134a, 152a, 227ea, and 32.

26. A method according to claim 1 wherein step (b) is further defined as measuring expired analytical gas concentrations in a plurality of breaths of the subject.

27. A method according to claim 26 wherein step (b) is further defined as measuring expired analytical gas concentrations in breaths occurring before recirculation of the blood occurs in the subject.

28. A method according to claim 1 further defined as determining the magnitude of pulmonary blood flow from the compartmental tidal volumes ($V_{ti}$) of the distribution and from ventilation/perfusion ratios.

29. A method according to claim 1 further defined as including the step of determining FRC of the subject's lungs using expired concentration measurements of one of the analytical gases.

30. A method according to claim 29 further defined as including the step of determining the amount of pulmonary tissue volume and lung water using expired concentration measurements of analytical gases of different solubilities.

31. A method according to claim 1 further defined as including the step of providing correction for the anatomical dead spaces of the subject.

32. A method for determining the distribution of the tidal volume ($V_t$) of gases inspired by a subject into his/her lungs, the distribution being among a plurality of compartments (i), each compartment having an assigned ratio value of a compartmental tidal volume ($V_{ti}$) to a compartmental perfusion ($Q_i$) and an assigned ratio value of the compartmental tidal volume ($V_{ti}$) to a compartmental volume ($V_{ai}$) so that the compartments, collectively, cover at least one of a range of ventilation/perfusion ratio ($V_t/Q$) values and a range of ventilation/volume ($V_t/V_a$) ratio values, said method comprising the steps of:

(a) causing the subject to inspire a bolus of analytical gases in a tidal volume of breathing gases, the analytical gases of the bolus having differing solubilities in the blood of the subject and being inspired in known amounts;

(b) measuring the concentrations of the analytical gases in the breathing gases expired by the subject for at least one breath of the subject;

(c) measuring the functional residual capacity of the lungs of the subject;

(d) expressing the expired concentrations of analytical gases in a form $$F_{exp}(\lambda,n)=(V_{bolus}/V_t^2)\Sigma_i V_{ti} g(x_i,y_i,\lambda,n) \quad (8)$$

where $$g(x_i,y_i,\lambda,n)=x_i/(x_i+1)^n \exp(-\lambda x_i n \Delta t/(y_i(x_i+1))) \quad (9)$$

wherein:

$F_{exp}$=expired analytical gas concentration
$V_{bolus}$=volume of analytical gas bolus
$V_t$=tidal volume
$V_{ti}$=compartmental tidal volume
$V_{ai}$=compartmental alveolar volume
$x_i$=compartmental ventilation/volume ratio, $V_{ti}/V_{ai}$
$y_i$=compartmental ventilation/perfusion ratio, $V_{ti}/Q_i$
$\lambda$=solubility
n=breath number
$\Delta t$=duration of breath (e) minimizing the expressions of step (d) using the method of Lagrange multipliers wherein a weight factor in the method of Lagrange multipliers relates to the functional residual capacity; and (f) solving the expressions of step (e) using a Monte Carlo simulation and satisfying the constraint $V_t => 0$ to obtain a compartmental tidal volume ($V_{ti}$) distribution among the compartments that represents a solution to the expressions of step (d).

33. A method for determining a distributive relationship in the lungs of a subject, the distribution occurring among a plurality of compartments (i) having at least one defined characteristic relating to tidal volume ($V_{ti}$) distribution, alveolar volume ($V_{ai}$) distribution, perfusion (Q) distribution, and ventilation/perfusion ($V_t/Q$), ventilation/volume ($V_t/V_a$), and perfusion/volume ($Q/V_a$) ratios, said method comprising the steps of:

(a) causing the subject to inspire a bolus of analytical gases in a tidal volume of breathing gases, the analytical gases of the bolus having differing solubilities in the blood of the subject and being inspired in known amounts;

(b) measuring the concentrations of the analytical gases in the breathing gases expired by the subject for at least one breath of the subject;

(c) expressing the expired concentrations of analytical gases in a form $$F_{exp}(\lambda,n)=(F_{bolus}/V_t^2)\Sigma_i V_{ti} g(x_i,y_i,\lambda,n) \quad (8)$$

where $$g(x_i,y_i,\lambda,n)=x_i/(x_i+1)^n \exp(-\lambda x_i n \Delta t/(y_i(x_i+1))) \quad (9)$$

wherein:

$F_{exp}$=expired analytical gas concentration
$V_{bolus}$=volume of analytical gas bolus $V_t$=tidal volume
$V_{ti}$=compartmental tidal volume
$V_{ai}$=compartmental alveolar volume
$x_i$=compartmental ventilation/volume ratio, $V_{ti}/V_{ai}$
$y_i$=compartmental ventilation/perfusion ratio, $V_{ti}/Q_i$
$\lambda$=solubility
n=breath number
$\Delta t$=duration of breath (d) dividing the lungs into compartments by setting at least one selected quantity or ratio of quantities in the expression to a set of selected values and allowing at least one of the variables in the expression to be the unknown for which a solution is sought; and (e) solving the expressions of step (c) to obtain a solution to the expressions of step (c).

34. A method according to claim 33 wherein step (d) is further defined as setting the compartmental ventilation/perfusion ($V_{ti}/Q_i$) and ventilation/volume ($V_{ti}/V_{ai}$) ratios to selected values and wherein step (e) is further defined as solving the expressions of step (c) for the compartmental tidal volume ($V_{ti}$) distribution.

35. A method according to claim 33 wherein step (d) is further defined as setting the compartmental tidal volumes ($V_{ti}$) at a selected value or values and wherein step (e) is further defined as solving the expressions of step (c) for the alveolar volume ($V_{ai}$) and compartmental perfusion ($Q_i$) distributions.

36. A method according to claim 33 wherein step (d) is further defined as setting the compartmental volumes ($V_{ai}$) at a selected value or values and wherein step (e) is further defined as solving the expressions of step (c) for the compartmental tidal volume ($V_{ti}$) and compartmental perfusion ($Q_i$) distributions.

37. A method according to claim 34 wherein step (d) is further defined as setting the compartmental perfusion ($Q_i$) at a selected value or values and wherein step (e) is further defined as solving the expressions of step (c) for the compartmental tidal volume ($V_{ti}$) and compartmental alveolar volume ($V_{ai}$) distributions.

* * * * *

UNITED STATES PATENT AND TRADEMARK OFFICE
CERTIFICATE OF CORRECTION

PATENT NO. : 6,254,546 B1
DATED : July 3, 2001
INVENTOR(S) : Viertiö-Oja

It is certified that error appears in the above-identified patent and that said Letters Patent is hereby corrected as shown below:

<u>Title page,</u>
Item [75], Inventors" delete "Hanna Vierto-Oja" and substitute therefor
-- Hanna Viertiö-Oja --

Signed and Sealed this

Seventh Day of May, 2002

Attest:

Attesting Officer

JAMES E. ROGAN
*Director of the United States Patent and Trademark Office*